United States Patent
Kadam et al.

(10) Patent No.: US 12,204,609 B1
(45) Date of Patent: Jan. 21, 2025

(54) TRAINING OF PREDICTIVE ARTIFICIAL INTELLIGENCE MODELS ACCEPTABILITY AND VALUE FEEDBACK LOOP

(71) Applicant: VARIAN MEDICAL SYSTEMS, INC., Palo Alto, CA (US)

(72) Inventors: Ashish Kadam, Maharashtra (IN); Roshan Joe Vincent, Atlanta, GA (US); Rakesh Sharma, Bangalore (IN); Petr Jordan, Palo Alto, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 1046 days.

(21) Appl. No.: 17/124,270

(22) Filed: Dec. 16, 2020

Related U.S. Application Data

(60) Provisional application No. 62/955,286, filed on Dec. 30, 2019.

(51) Int. Cl.
| | |
|---|---|
| G06F 18/214 | (2023.01) |
| G06F 8/71 | (2018.01) |
| G06F 18/21 | (2023.01) |
| G06N 20/00 | (2019.01) |
| G16H 40/20 | (2018.01) |

(52) U.S. Cl.
CPC .......... *G06F 18/2148* (2023.01); *G06F 8/71* (2013.01); *G06F 18/2178* (2023.01); *G06N 20/00* (2019.01); *G16H 40/20* (2018.01)

(58) Field of Classification Search
None
See application file for complete search history.

(56) References Cited

U.S. PATENT DOCUMENTS

| | | | | |
|---|---|---|---|---|
| 2014/0032436 A1* | 1/2014 | Patel | ................ | G06Q 10/1053 |
| | | | | 705/321 |
| 2015/0332169 A1* | 11/2015 | Bivens | ................ | G06N 20/00 |
| | | | | 706/12 |
| 2018/0144244 A1* | 5/2018 | Masoud | ................ | G06N 3/105 |
| 2018/0204325 A1* | 7/2018 | Steigauf | ................ | G06F 18/2148 |
| 2019/0220975 A1* | 7/2019 | Hsieh | ................ | G06N 3/08 |
| 2019/0392942 A1* | 12/2019 | Sorenson | ................ | G06F 40/30 |
| 2020/0042832 A1* | 2/2020 | Kim | ................ | G06F 18/217 |
| 2020/0211692 A1* | 7/2020 | Kalafut | ................ | G06N 20/00 |
| 2020/0311541 A1* | 10/2020 | Cmielowski | ................ | G06N 3/04 |
| 2021/0073627 A1* | 3/2021 | Sarferaz | ................ | G06N 3/08 |

* cited by examiner

*Primary Examiner* — Philip J Chea
*Assistant Examiner* — Bin Qing Zheng
(74) *Attorney, Agent, or Firm* — Foley & Lardner LLP

(57) ABSTRACT

Disclosed herein are methods and systems for training artificial intelligence (AI) models. A central server may train an AI model by outputting, onto an electronic device operated by a user, results of execution of the AI model; monitoring the electronic device to identify a set of interactions between the user and the electronic device while the electronic device is outputting the results; generating a first training dataset corresponding to the user's interactions with the electronic device, the first training dataset corresponding to a frequency of correction of results; generating a second training dataset corresponding to the user's input to a prompt requesting the user to input a numerical value associated with an accuracy of the results; and training the AI model using the first and second training datasets.

17 Claims, 6 Drawing Sheets

TRAINING OF PREDICTIVE ARTIFICIAL INTELLIGENCE MODELS ACCEPTABILITY AND VALUE FEEDBACK LOOP

CROSS REFERENCE TO RELATED APPLICATIONS

This application claims priority to U.S. Provisional Application No. 62/955,286, filed on Dec. 30, 2019, which is incorporated by reference herein in its entirety and for all purposes.

TECHNICAL FIELD

This application relates generally to generating, training, and operating artificial intelligence models to achieve better results.

BACKGROUND

A vast majority of today's artificial intelligence (AI) models in healthcare are trained on datasets representing only a limited distribution of the patient population. FIG. 3 represents a conventional AI training method. As depicted, an AI system may produce predicted results and a training module may use existing data known to be accurate (e.g., ground truth) to train the AI model. However, since the implementation of these AI training methods, a few technical challenges have been identified.

AI models trained using conventional methods tend to perform poorly when encountering data from another population, resulting in suboptimal prediction accuracy and time burden to correct inaccurate model predictions. This limitation stems from the fact that predictive models are typically trained using loss functions (e.g., the Dice similarity index, cross-entropy, mean squared difference, mean absolute difference) calculated from retrospective data. Performance and accuracy requirement most pertinent to clinical adoption are typically not directly included in the loss function used to train a model.

SUMMARY

For the aforementioned reasons, there is a desire for an improved AI modeling/training technique that does not rely solely on retrospective data or loss functions. There is a desire for methods and systems to train AI models using dynamic and selectable segmentations of users. There is a desire for methods and systems to train AI models not based on aggregated data acceptable to administrators but based on end user's practical usage and acceptance of the results. What is desired is an AI modeling/training technique that is more efficient and produces results that are more accurate. The methods and systems described herein produce results that adapt to usage patterns and acceptability requirements of model consumers (e.g., clinical users).

In one embodiment, a method for training an artificial intelligence model comprises outputting, by a server onto an electronic device operated by a user, results of execution of an artificial intelligence model; monitoring, by the server, the electronic device to identify a set of interactions between the user and the electronic device while the electronic device is outputting the results; generating, by the server, a first training dataset corresponding to the user's interactions with the electronic device, the first training dataset corresponding to at least one of a frequency of correction of results, a time period associated with the user interacting with the results, and a ratio of the results modified by the user; generating, by the server, a second training dataset corresponding to the user's input to a prompt requesting the user to input a numerical value associated with an accuracy of the results; and training, by the server, the artificial intelligence model using the first and second training datasets.

In another embodiment, a computer system for training an artificial intelligence model, the computer system comprises an electronic device configured to output results of execution of the artificial intelligence model; and a server communicatively coupled with the electronic device, the server configured to output, onto an electronic device operated by a user, results of execution of the artificial intelligence model; monitor the electronic device to identify a set of interactions between the user and the electronic device while the electronic device is outputting the results; generate a first training dataset corresponding to the user's interactions with the electronic device, the first training dataset corresponding to a frequency of correction of results; generate a second training dataset corresponding to the user's input to a prompt requesting the user to input a numerical value associated with an accuracy of the results; and train the artificial intelligence model using the first and second training datasets.

In yet another embodiment, a machine-readable storage medium having computer-executable instructions stored thereon that, when executed by one or more processors, cause the one or more processors to perform operations comprises outputting, onto an electronic device operated by a user, results of execution of the artificial intelligence model; monitoring the electronic device to identify a set of interactions between the user and the electronic device while the electronic device is outputting the results; generating a first training dataset corresponding to the user's interactions with the electronic device, the first training dataset corresponding to a frequency of correction of results; generating a second training dataset corresponding to the user's input to a prompt requesting the user to input a numerical value associated with an accuracy of the results; and training the artificial intelligence model using the first and second training datasets.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
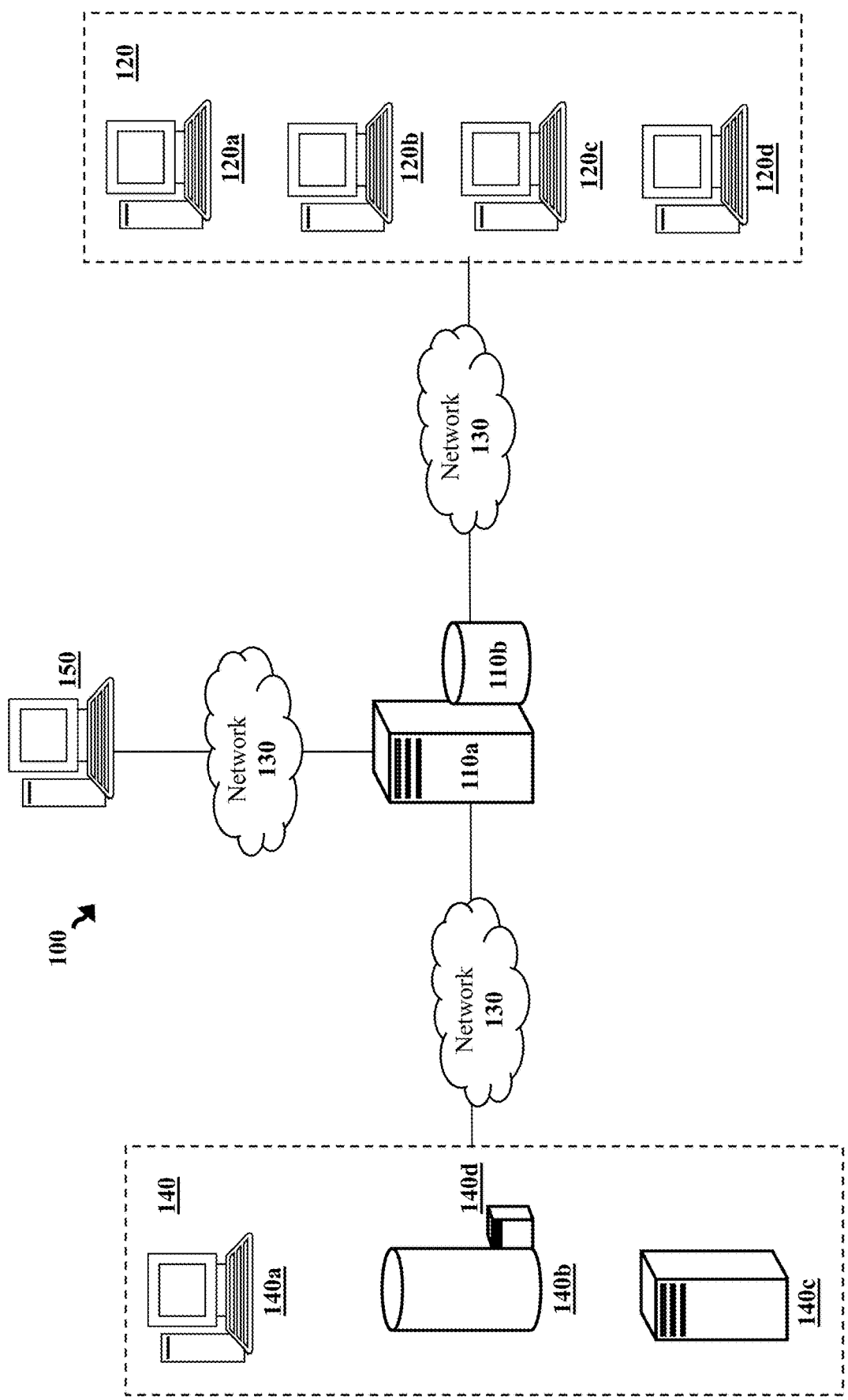
FIG. 1 illustrates components of an artificial intelligence (AI) training system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

The methods and systems described herein provide a mechanism for model improvement based on feedback loops. The methods and systems described herein incorporate clinical model performance using a meta-training feedback loop consisting of an automatic model training pipeline, a data catalog, and intelligent methods for automatic incorporation of informative data points based on clinical use.

Conventionally, predictive models are trained using loss functions, which calculates the difference between predicted and ground truth labels, iteratively updates model weights/parameters, and improves predictions. When traditional continuous training is used, the model is trained incrementally on new data and improves its generalizability to new patient distributions. In contrast, the methods and systems described herein (e.g., system 100 depicted in FIG. 1) use direct clinical feedback from the end user in a training loop, which consequently results in training models that are optimized for clinical acceptability and value. Furthermore, these methods and systems allow for training models that are customized to user preferences or clinical protocol needs. Disclosed training system can be fully automated, enabling scalability across clinical practices, geographical locations, and wide range of clinical preferences.

The feedback loop described herein may involve incorporation of the clinical user's direct interactions with the model (e.g., frequency of model acceptance, amount of time spent on correcting model predictions, and/or amount of structure volume modified by the user). Additionally or alternatively, the feedback loop may involve qualitative assessment from the user (e.g., asking the user to rate the model on a numerical scale or even a binary scale such as thumbs up/thumbs down). Additionally or alternatively, the feedback loop may involve and incorporate the user's clinical "credibility score," and increase the feedback weight/importance based on the user's performance amongst his or her peers. AI models trained using clinical usage feedback will result in higher user satisfaction and increased productivity.

The AI training methods described above can be implemented using sig various system architectures and electronic infrastructures. FIG. 1 illustrates components of an AI training system 100 that can be used to iteratively train an AI model using the methods described herein. The system 100 may include an analytics server 110a, system database 110b, user computing devices 120a-d (collectively, user computing devices 120), electronic data sources 140a-c (collectively, electronic data source 140), and an administrator computing device. The above-mentioned components may be connected to each other through a network 130. The examples of the network 130 may include, but are not limited to, private or public LAN, WLAN, MAN, WAN, and the Internet. The network 130 may include both wired and wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets, or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or alternate components, not shown for brevity, which are to be considered within the scope of the embodiments described herein.

The analytics server 110a may generate and display an electronic platform configured to use various AI models to display predicted results. The electronic platform may include graphical user interface (GUI) displayed on each user computing device 120. An example of the electronic platform generated and hosted by the analytics server 110a may be a web-based application or a website configured to be displayed on different electronic devices, such as mobile devices, tablets, personal computer, and the like (e.g., computing devices 120).

The analytics server 110a may host a website accessible to end users, where the content presented via the various webpages may be controlled based upon each particular user's role or viewing permissions. The analytics server 110a may be any computing device comprising a processor and non-transitory machine-readable storage capable of executing the various tasks and processes described herein. Non-limiting examples of such computing devices may include workstation computers, laptop computers, server computers, laptop computers, and the like. While the system 100 includes a single analytics server 110a, in some configurations, the analytics server 110a may include any number of computing devices operating in a distributed computing environment.

The analytics server 110a may execute software applications configured to display the electronic platform (e.g., host a website), which may generate and serve various webpages to each user computing device 120. Different users operating the user computing devices 120 may use the website to view and/or interact with the predicted results.

In some implementations, the analytics server 110a may be configured to require user authentication based upon a set of user authorization credentials (e.g., username, password, biometrics, cryptographic certificate, and the like). In such implementations, the analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may also store data associated with each user operating one or more computing devices 120. The analytics server 110a may use the data to weigh interaction while training various AI models accordingly. For instance, the analytics server 110a may generate a score for each user and a respective weight for their respective inputs accordingly. The data associated with each user may include but not limited to, demographic data (e.g., age, degree, income, sex, and employer) or skill-based data (e.g., degree, experience, and title).

In some configurations, the analytics server 110a may generate and host webpages based upon a particular user's role within the system 100 (e.g., administrator, employee, and/or bidder). In such implementations, the user's role may be defined by data fields and input fields in user records stored in the system database 110b. The analytics server 110a may authenticate the user and may identify the user's role by executing an access directory protocol (e.g., LDAP). The analytics server 110a may generate webpage content that customized according to the user's role defined by the user record in the system database 110b.

In some embodiments, the analytics server 110a receives information from a user (or retrieve from a data repository), analyzes the data, and displays the results (e.g., AI-based results) on the electronic platform. For instance, in a non-limiting example, a user operating the computing device 120b uploads an image of a CT scan or other medical images using the electronic platform. The analytics server 110a then use various AI models (stored within the system database 110b) to analyze the uploaded image. The analytics serve 110a then displays the results (e.g., size and shape of a tumor) via the electronic platform.

User computing devices 120 may be any computing device comprising a processor and a non-transitory machine-readable storage medium capable of performing the various tasks and processes described herein. Non-limiting examples of a network node may be a workstation computer, laptop computer, tablet computer, and server computer. In operations, various users may use computing devices 120 to access the GUI operationally managed by the analytics server 110a.

The electronic data sources 140 may represent various electronic data sources that contain data associated with external data sources. For instance, database 140c and third-party server 140b may represent data sources providing the corpus of data (e.g., images) needed for the analytics server 110a to train one or more AI models.

The administrator computing device 150 may represent a computing device operated by a system administrator. The administrator computing device 150 may be configured to display various analytic metrics where the system administrator can monitor the AI training, review feedback, and modify various thresholds/rules described herein.

In operation, the analytics server 110a may train an AI model using ground truth data retrieved from the electronic data sources 140. The analytics server 110a may then receive a request from the user computing device 120 to analyze data. In response, the analytics server 110a may execute the trained AI model and display predicted results onto the user computing devices 120. The analytics server 110a may then monitor the users' interactions with the predicted results and may retrain the AI model accordingly.

Figure 2:
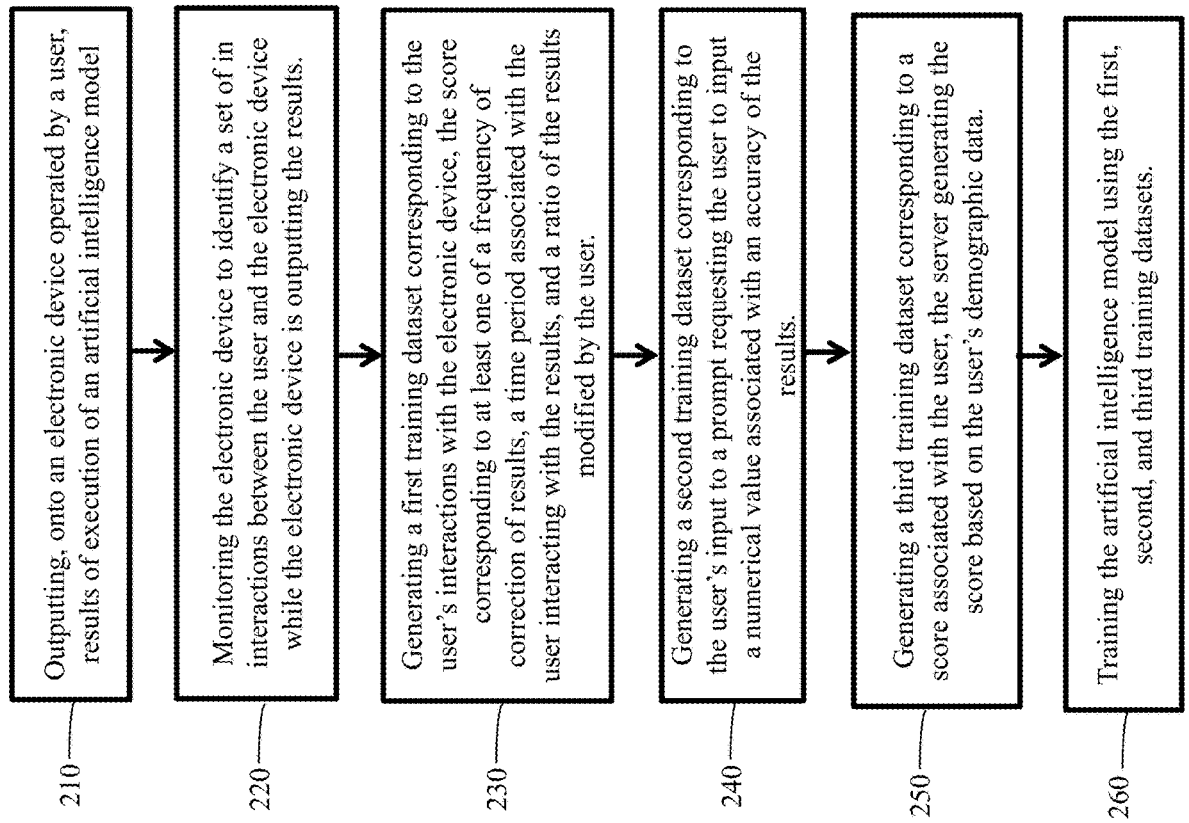
FIG. 2 illustrates a flow diagram of a process executed in an AI training system, according to an embodiment.
Figure 3:
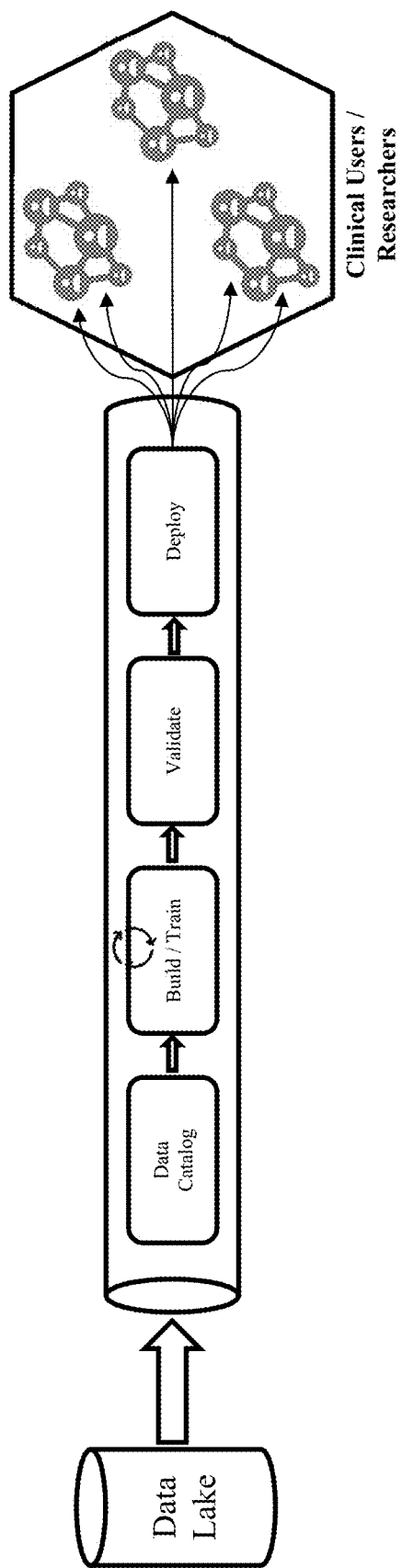
FIG. 3 illustrates a conventional method of training AI models, according to an embodiment.

FIG. 2 illustrates a flow diagram of a process executed in an AI training system, according to an embodiment. The method 200 includes steps 210-260. However, other embodiments may include additional or alternative execution steps, or may omit one or more steps altogether. The method 200 is described as being executed by a server, similar to the analytics server described in FIG. 1. However, one or more steps of method 200 may also be executed by any number of computing devices operating in the distributed computing system described in FIG. 1. For instance, one or more user computing devices may locally perform part or all of the steps described in FIG. 2.

Even though some aspects of the embodiments described herein are described within the context of clinical and healthcare-specific software, it is expressly understood that methods and systems described herein apply to all AI models and training techniques. For instance, in other embodiments, the methods and systems described herein may be applied to an AI model that is configured to predict whether users will attend their scheduled appointments.

At step 210, the analytics server may output, onto an electronic device operated by a user, results of execution of an artificial intelligence model. The analytics server may execute an AI model to satisfy a request received from an electronic device operated by a user. For instance, a user may upload an image via an electronic platform generated and operated by the analytics server. The user may request the analytics server to execute AI models and predict various attributes associated with the uploaded image, such as predicted volume and measurements of the uploaded image. The analytics server may execute an AI model using the received data and output (e.g., display) the predicted results.

At step 220, the analytics server may monitor the electronic device to identify interactions between the user and the electronic device while the electronic device is outputting the results. When the analytics server outputs the predicted results onto one or more user electronic devices, the analytics server may monitor the user's interactions with the results. As will be described below, the analytics server may then train the AI model based on the monitored data.

When the user performs an activity on the electronic platform, the analytics server may track and record details of the user's activity. For instance, when a predicted result is displayed on the user electronic device, the analytics server may monitor to identify whether the user has interacted with the predicted results by editing, deleting, accepting, or revising the results. The analytics server may also identify a timestamp of each interaction, such that the analytics server records the frequency of modification, duration of revision/correction.

The analytics server may utilize an application programming interface (API) to monitor the user's activities. The analytics server may use an executable file to monitor the user's electronic device. The analytics server may also monitor the electronic platform displayed on an electronic device via a browser extension executing on the electronic device. The analytics server may monitor multiple electronic devices and various applications executing on the electronic devices. The analytics server may communicate with various electronic devices and monitor the communications between the electronic devices and the various servers executing applications on the electronic devices.

In some embodiments, the analytics server may monitor the data packages received and sent by each electronic device to monitor the content of what is displayed/executed/modified on the electronic device. The communication may take any suitable form. For example, the electronic device may execute an application (e.g., browser extension) having an executable file that enables a user to navigate to the electronic platform (e.g., web site).

The analytics server may use several techniques to track user's activities on the electronic device, such as by tracking browser cookies and/or screen-scraping protocols. In another example, the analytics server may track the user activity by periodically retrieving user's web browser cookies. The analytics server may transmit cookies to a system database where they can be analyzed (e.g., in batches) to identify user activities.

In some configurations, the analytics server may monitor the electronic device using an executable file (application) installed as a browser extension. The browser extension (executable file) may be executed as a background process of the electronic device. For instance, the browser extension may be transparent to the user operating the electronic device. In this way, the analytics server is able to monitor the user's activities without disturbing the user and/or obfuscating the display screen of the electronic device. In some embodiments, the analytics server may activate a monitoring module (e.g., browser extension or executable file) upon outputting the results on the electronic platform.

The analytics server may use the data collected/monitored to train the AI model and improve its predicted results. In order to train the AI model, the analytics server may generate three separate training datasets (steps 230-250). The analytics server may use one or more of these training datasets to train the AI model. The analytics server may use the generated training datasets to relabel the data where the relabeled data is ingested by the AI model for retraining purposes.

At step 230, the analytics server may generate a first training dataset corresponding to the user's interactions with the electronic device, the first training dataset corresponding to at least one of a frequency of correction of results, a time duration associated with the user interacting with the results, and a ratio of the results modified by the user.

The first training dataset may include data corresponding to direct user interactions with the electronic platform. The first training dataset may include the following categories of data: model acceptance frequency, time spent of model correction, the correction of data, and predicted volume of modification.

Model Acceptance Frequency

The analytics server may monitor whether an end user accepted the predicted results. The analytics server may generate a metric corresponding to a frequency that a certain predicted result was accepted, denied, or revised. If the predicted results were accepted, the analytics server assumes that the predicted results were satisfactory to the end user. If the user revised the predicted results, the analytics server assumes that they were partially satisfactory to the user. Finally, if the user denied the predicted results, the analytics server assumes that they were completely unsatisfactory. The analytics server may then generate a score/metric that corresponds to these three options. For instance, the analytics server may assign 1 point when a result is accepted, 0.5 point to revised results, and 0 point for denied results. The analytics server may then train the AI model accordingly. For instance, the analytics server may relabel the predicted results using the scoring scheme described above and may retrain the AI model.

The analytics server may also generate a score for how frequently predicted results generated by a model is accepted, revised, and/or denied. For instance, if an AI model produces results that are denied/revised 80% of the time, then the analytics server may generate a low score for the AI model. If the AI model produces results that is revised/denied 20% of the time, then the analytics server may generate a higher score for the AI model.

Time Spent of Model Correction

As described above, when a user revises a predicted result, the analytics server monitors the revision performed by the user. In some embodiments, the analytics server displays a predicted result on the electronic platform. However, the users feel the need to perform minor corrections before they are satisfied with the results. The analytics server may monitor this correction and generate training datasets accordingly. For instance, the analytics server may monitor a time duration that each user spent correcting the predicted results. The analytics server may assume that a higher this monitored time duration corresponds to, more inaccurate the results.

In some embodiments, the analytics server may also monitor the corrections implemented by the users. For instance, in a non-limiting example of using AI for image recognition, the analytics server monitors whether users revised the predicted size of a tumor or another organ (e.g., predicted result). The analytics server may then generate a score that corresponds to the revisions. For instance, when a predicted tumor size if revised by 20%, the analytics server assigns a higher score than when a user revises the predicted tumor size by 50%. The analytics server assumes that fewer revisions (more minor) implemented by users corresponds to a better-predicted results.

Predicted Volume of Modification

The analytics server may measure various specific factors associated with the revisions, such as volume of change, color changed, area of the revisions, and the like. In some configurations, the analytics server may use predetermined scoring rules to normalize and quantify the revisions. This standardization allows the analytics server to use normalized and uniform data to train the AI across various platforms and for different users or segmentations of users.

At step 240, the analytics server may generate a second training dataset corresponding to the user's input to a prompt requesting the user to input a numerical value associated with an accuracy of the predicted results.

The analytics server may display a prompt requesting the users to provide feedback regarding the predicted results outputted by the analytics server. For instance, the analytics server may display a prompt having an input element (e.g., text string input, drop down menu, radio button). The end user may interact with the prompt to input a feedback regarding the accuracy of the results outputted by the analytics server.

The feedback provided by the users may be a binary and/or a numerical input. For instance, the analytics server may provide a simple "thumbs up/thumbs down" prompt where the user can rate the accuracy of the results using a binary scale. In some embodiments, the analytics server may request the user to input a number within a predetermined scale that represents the accuracy of the results (e.g., 0-10 scale). The analytics server may then collect the feedback data and generate the second set of training data accordingly.

The analytics server displays the prompts on the electronic user devices based on various predetermined rules and criteria. For instance, in some embodiments, the analytics server may always display a prompt requesting users' feedback. In some embodiments, the analytics server may display the prompt based on a predetermined frequency (e.g., 50% of instances where a predicted result is displayed). Furthermore, the analytics server may select the users receiving the prompt based on predetermined rules. For instance, the analytics server may select the users randomly. In some configurations, the predetermined rules may require the analytics server to display the prompt for users who satisfy a certain threshold (e.g., only for users who have three or more years of experience).

In some configurations, the analytics server only displays the prompt when the displayed predicted results satisfy a threshold. For instance, the analytics server may only display the prompt when the results correspond to AI-enabled image processing or only when the end user revises a predicted result. A system administrator can modify all the predetermined rules and threshold. The system administrator can also customize the predetermined rules and thresholds, such that the analytics server displays the prompts to a customized set of users for a customized set of results. For instance, a predetermined set of rules may require the analytics server to display the prompt asking a thumbs up/thumbs down feedback for doctors with more than two years of experience when the results corresponds to cancer diagnosis.

At step 250, the analytics server may generate a third training dataset corresponding to a score associated with the user, the server generating the score based on the user's demographic data.

The analytics server may generate a score for each user providing the feedback. The score may be based on a set of predetermined rules. The analytics server may generate the score based on a user's credibility and/or user's performance in comparison to his/her peers. For instance, the analytics server may periodically monitor users and update their demographic and/or professional data. The analytics server may then use various inputted and/or predetermined thresholds to generate a score for each user. For instance, the analytics server may assign a higher score to a medical doctor than a nurse.

As discussed above, the analytics server may periodically update user data. Therefore, the score may evolve as the user evolves and professionally grows. In some embodiments, the analytics server weigh feedback received from the users based on their score. The analytics server may prioritize feedback from users with higher scores. The score for each user may also correspond to a credibility of a user with regard to training the AI model. For instance, a user with a higher score may be deemed more credible than other users.

The analytics server may also generate the score based on other user's feedback and credibility. For instance, the analytics server may rank the users (within a clinic or any other predefined data segmentation). The analytics server may then assign a score according to this rank. In some embodiments, the analytics server may request feedback from other users regarding a particular user and may assign the score accordingly. In this way, if a user has an objectively low score but subjectively scores high within other users, the analytics server may still use the user's feedback to train the AI model.

In some embodiments, the analytics server may use one or more scores to segment/filter the training datasets and to train the AI model. For instance, the analytics server may only train the AI model using feedback received from users who satisfy a score threshold. In some configurations, the analytics server may weigh the feedback data received from users in accordance with their respective score. For instance, the analytics server may use all the feedback data received. However, the training may be weighted based on the user providing the feedback. In this way, the analytics server may use the third training dataset in conjunction with one or both the first and second training datasets.

In some embodiments, the score may represent a range corresponding to each user's ability that is much broader than user's demographics. For instance, the score may be calculated from the users' historical performance, their reputation amongst peers, etc.

At step 260, the analytics server may train the AI model using the first, second, and third training datasets. The analytics server may train the AI model using one or more training datasets described above. The analytics server may use various methods to train the AI model, such as supervised and/or unsupervised learning methods. For instance, the analytics server may use one or more of the following machine learning approaches to train the AI model: regression, classification, clustering, dimensionality reduction, ensemble methods, neural nets and deep learning, transfer learning, reinforcement learning, and the like.

In some embodiments, the analytics server may periodically train the AI model. For instance, the analytics server may collect/monitor user interactions and store the corresponding data. The analytics server may then use a predetermined frequency (e.g., once a month or once a week) to train the AI model using the stored training datasets. A system administrator can modify the frequency of the batch training.

Additionally or alternatively, the analytics server may have other "triggering" conditions to train the AI model. For instance, the analytics server may continuously compare the results of execution of the AI model with a ground truth. The analytics server may then train the AI model using the training datasets when the analytics server determines that the results generated by the AI model are incorrect or satisfy a threshold with respect to the ground truth. In a non-limiting example, the analytics server may train the AI model when the analytics server identifies that the results generated by the AI model are incorrect by a predetermined threshold (e.g., at least 8% difference between a ground truth and the results generated by the AI model).

Additionally or alternatively, the analytics server may implement safeguards to ensure that training the AI model is conducted in an acceptable manner. As discussed above, the analytics server may generate the training datasets based on predefined criteria to ensure that the models are trained based on feedback received from users that satisfy certain criteria (e.g., more credible/experienced users). In another example, the analytics server may implement a manual review where a system administrator may review the feedback data. The analytics server may display a prompt onto one or more system administrator's computers and request the system administrators to review the feedback data before the feedback data is included in the training datasets.

Additionally or alternatively, the analytics server may train the AI model when the AI model produces results that receive feedback that satisfies a threshold. For instance, the analytics server trains the AI model when the results outputted on the electronic platform receive a feedback (e.g., thumbs down or modification/revision of the results by the users) more frequently than a predefined threshold (e.g., 40% of time).

Additionally or alternatively, the analytics server may train the model based on a customized (predetermined) segmentation of training data and/or users. For instance, the analytics server may segment the training data before training the AI model. The analytics server may train the AI model in a customized and segmented manner that is meaningfully tethered to the end users' needs. In a non-limiting example, the analytics server may train the AI model based on feedback received from a selection of users (e.g., users who work at a particular clinic or users who satisfy a certain score). As a result, the analytics server may customize the AI model for a particular clinic. This training method allows the AI model to adapt to the particular clinic and produce results that are more acceptable to the users within that clinic.

Similar to all the thresholds, rules, and predetermined protocols described herein, the segmentation may be predefined but modifiable by a system administrator. Therefore, a system administrator may monitor the training of the AI model and modify the training, such that the training is applicable to a particular facility/clinic or the training only uses a segment of training data produced by a customized segment of the users.

In some configurations, the analytics server may implement various methods to conclude the training. The analytics server may use predetermined criteria and/or threshold to stop the training. For instance, when the results produced by the AI model satisfy a threshold (e.g., 20% different from a predefined ground truth), the analytics server may stop training the AI model. The analytics server may then revert to a previous version of the AI model (before the AI model was trained using feedback data). In some embodiments, the analytics server may completely isolate the AI model from the system, such that the AI model's results are no longer outputted by the system. In effect, the analytics server may force the AI model to be offline until and unless the analytics server further verifies whether the newly trained AI model satisfies various quality control standard and criteria.

Using the above-described safeguarding methods and systems, the analytics server may combat bias and other unwanted factors to be included in the training data, which would ultimately generate unwanted/inaccurate results.

Figure 4:
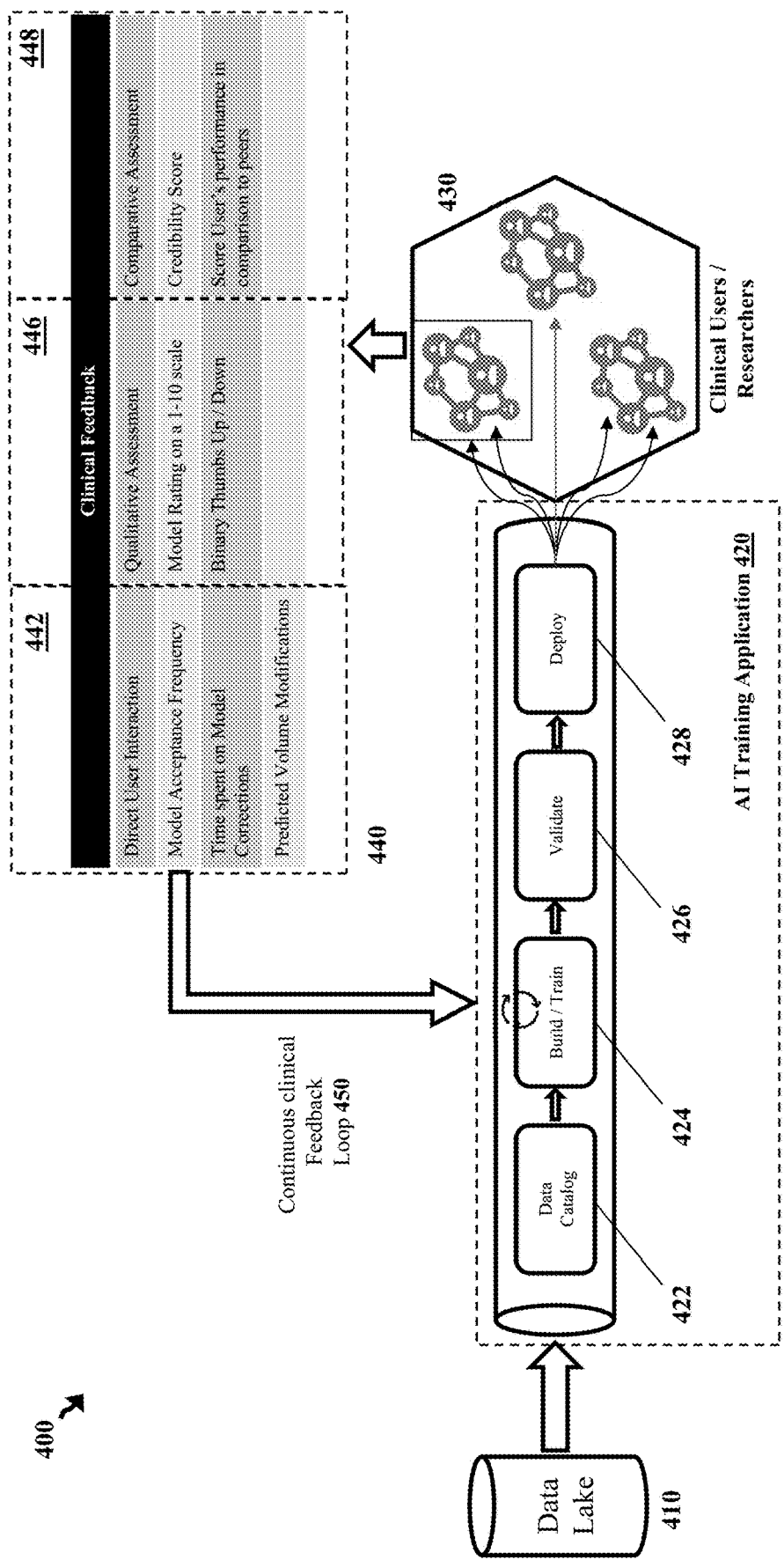
FIG. 4 illustrates a method of training AI models, according to an embodiment.

FIG. 4 illustrates a schematic design of a system that produces AI-generated predicted results and trains the AI model according to the methods and systems described herein, in accordance with an embodiment. As will be understood by a person skilled in the art, various reconfigurations of the modules/features described in this figure may be achieved without deviating from the scope of the method/systems described herein.

As illustrated in the embodiment 400, an AI training application 420 executed by at least one processor of one or more servers (e.g., the analytics server) may retrieve data from an electronic data repository (e.g., Data Lake 410), train, and execute one or more AI models. As a result, the AI training application 420 may display predicted results on an electronic platform accessible to clinical users/researchers 430.

The AI training application 420 may include multiple software modules configured to perform different tasks described herein. Even though the AI training application 420 is described as having different modules, it is expressly understood that a single server, such as the analytics server discussed in FIGS. 1-2 can act as the AI platform (training application) and all its modules. In some configurations, different servers and/or processors may perform different portions of the tasks described herein. For instance, tasks associated with the data catalog module 422 may be performed by one server and tasks associated with validate module 426 may be performed by another server. These servers are collectively referred to herein as the AI training application, AI platform, and/or the analytics server.

Even though aspects of the tasks described herein are depicted and described in a particular order, it is expressly understood that different actions and tasks described herein can be performed at different times and in different orders. For instance, indexing the data can be performed periodically and continuously regardless of how often the AI training application 420 trains the AI model.

The process of training the data may begin with the data catalog module 422 indexing data retrieved from the data lake 410 and transmitting the processed data to a build/train module 424. The build/train module 424 may first use the retrieved data to train an AI model. For instance, the build/train module may use known data (e.g., data associated with previous users or clinical research or other known data) to build and initially train an AI model. The AI model may be initially trained using various know AI training methods. The validate module 426 may then execute the initially trained AI model to generate predicted results and validate the predicted results using various known methods (e.g., comparing to ground truth or other predetermined criteria/rules, such as recall and/or precision validation methods). When the AI training application 420 validates the results generated by the AI model, the AI training application 420 utilizes a deploy module 428 to output the results onto an electronic platform where users (e.g., clinical users and/or researchers 430) can view and interact with the results. The deploy module 428 may either directly display the results or transmit the predicted results to another software system to be displayed for the clinical users and researchers 430.

In response to outputting the predicted results, the users may accept the results, deny the results, or revise the results. When the AI training application 420 displays the results, the AI training application 420 also initiates a monitoring protocol to identify how the users have interacted with the results. The AI training application 420 then generates training data accordingly. The data generated may be divided into three categories: direct user interactions, qualitative assessment, and comparative assessment of data. These categories correspond to different training datasets described in FIG. 2 and are depicted in the chart 440. The AI training application 420 may generate a training dataset for each category depicted in the chart 440. For instance, the AI training application 420 may generate a first dataset corresponding to data category 442, a second dataset corresponding to the data category 446, and a third dataset corresponding to the data category 448.

The AI training application 420 may use one or more training datasets to train the AI model. The AI training application 420 may transmit one or more of the training datasets back into the build/train module 424 (e.g., continuous clinical feedback loop 450). The AI training application 420 may then train the AI model using the newly acquired training datasets. In some configurations, the AI training application 420 may also use additional data retrieved from the data lake 410. For instance, the AI training application 420 may retrieve new data used to train the AI model (e.g., newly retrieved patient data and previously implemented treatments or other clinical data).

In the next iteration, the AI training application 420 may use a subsequent version of the AI model (trained via the method described above) to produce new results. The above-described process may be repeated and the AI training application 420 may retrain the AI model using the continuous clinical feedback loop 450. The AI training application 420 may iteratively retrain the AI model and generate a new version each time the AI model is trained and/or the results are outputted. In this way, the AI model trains itself and evolves as the users (e.g., clinical users and researchers 430) continue interacting with the results. Furthermore, the training method 400 allows the AI model to adapt and customize its predicted outcome to its respective end users. Therefore, the same model can be tailored towards the need of different end users (e.g., clinics).

Figure 5:
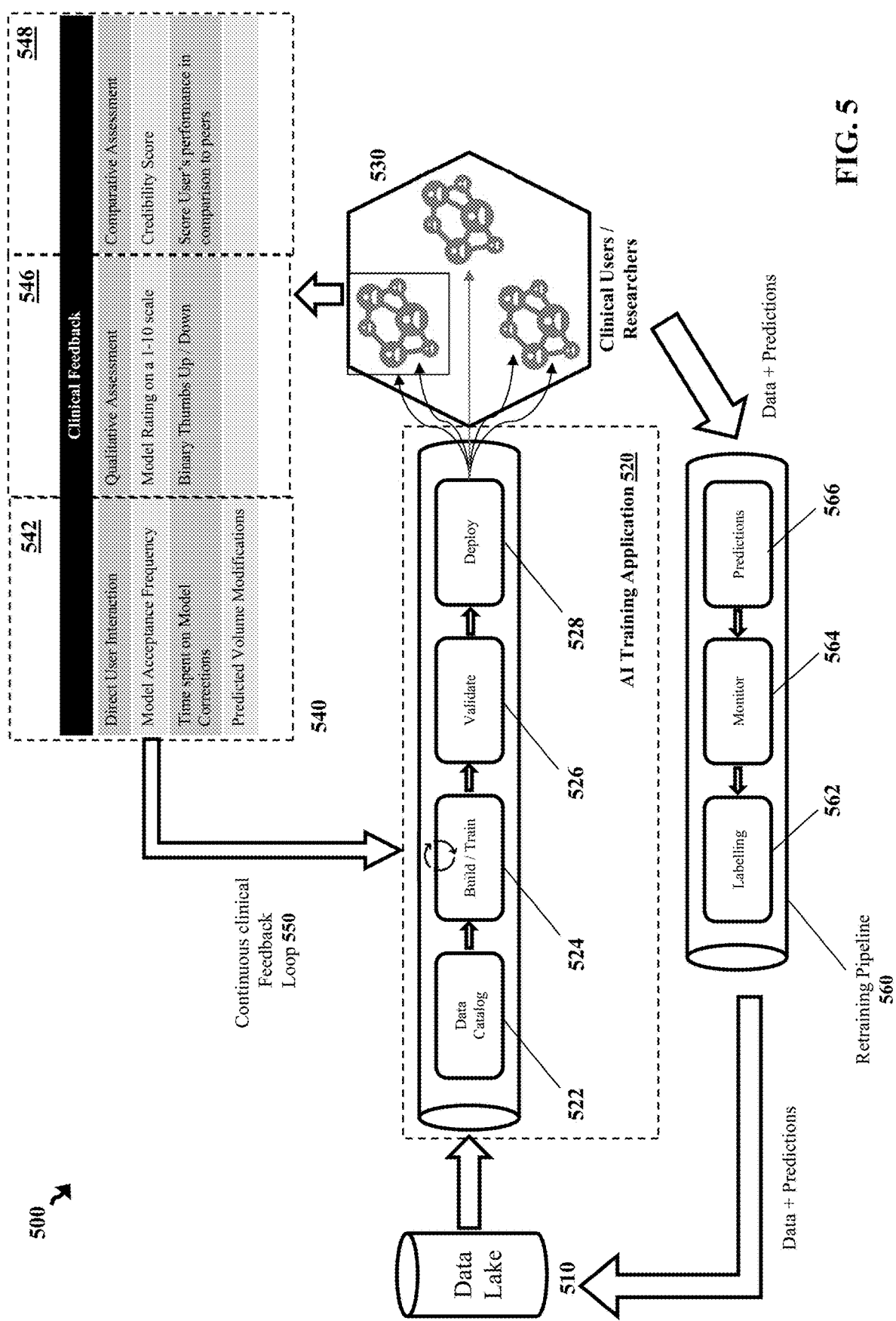
FIG. 5 illustrates a method of training AI models, according to an embodiment.

FIG. 5 illustrates an embodiment 500 where the analytics server uses a continuous feedback loop training method in conjunction with other AI training methods. For instance, the AI training application 520 displayed in FIG. 5 iteratively trains (and retrains) the AI model using a method similar to the method described in FIGS. 2 and 4. The AI training application 520 may then augment the training using the retraining pipeline 560.

As described above, the AI training application 520 may utilize a continuous clinical feedback loop 550 to iteratively train (and re-train) the AI model. Therefore, features 510-550 are similar to the features 410-450 described in FIG. 4. In addition to the continuous clinical feedback loop 550, the AI training application 520 may also use a retraining pipeline 560 where the predicted outcome is compared against the ground truth and the AI model is trained accordingly (e.g., loss function). For instance, the retraining pipeline 560 may use the data predicted by the trained AI model (and displayed on one or more platforms where clinical researchers 530 can interact with the results) to augment the continuous clinical feedback loop 550.

Additionally or alternatively, the retraining pipeline 560 may use the predictions module 566 to execute the trained AI model and generate results. The retraining pipeline 560 may then utilize the monitor module 564 and the labeling module 562 to evaluate the predicted results and generate a proper label associated with the predicted results. The retraining pipeline 560 may then transmit the labeled data in addition to the predicted data/results back into the data like 510 where the labeled data and the predicted data/results are aggregated and used by the AI training application 520 to retrain the AI model.

Even though the retraining pipeline 560 is depicted as a separate process not performed by the AI training application 520, it is expressly understood that a single server (e.g., the analytics server) can perform the functionality attributed to the AI training application 520 and the retraining pipeline 560. Furthermore, even though the retraining pipeline 560 is described as having different modules, it is expressly understood that a single server, such as the analytics server can act as the retraining pipeline 560 and all its modules. In some configurations, different servers and/or processors may perform different portions of the tasks described herein. For instance, tasks associated with the predictions module 566 may be performed by one server and tasks associated with the monitor module 564 and/or the labeling module 562 may be performed by another server.

Figure 6:
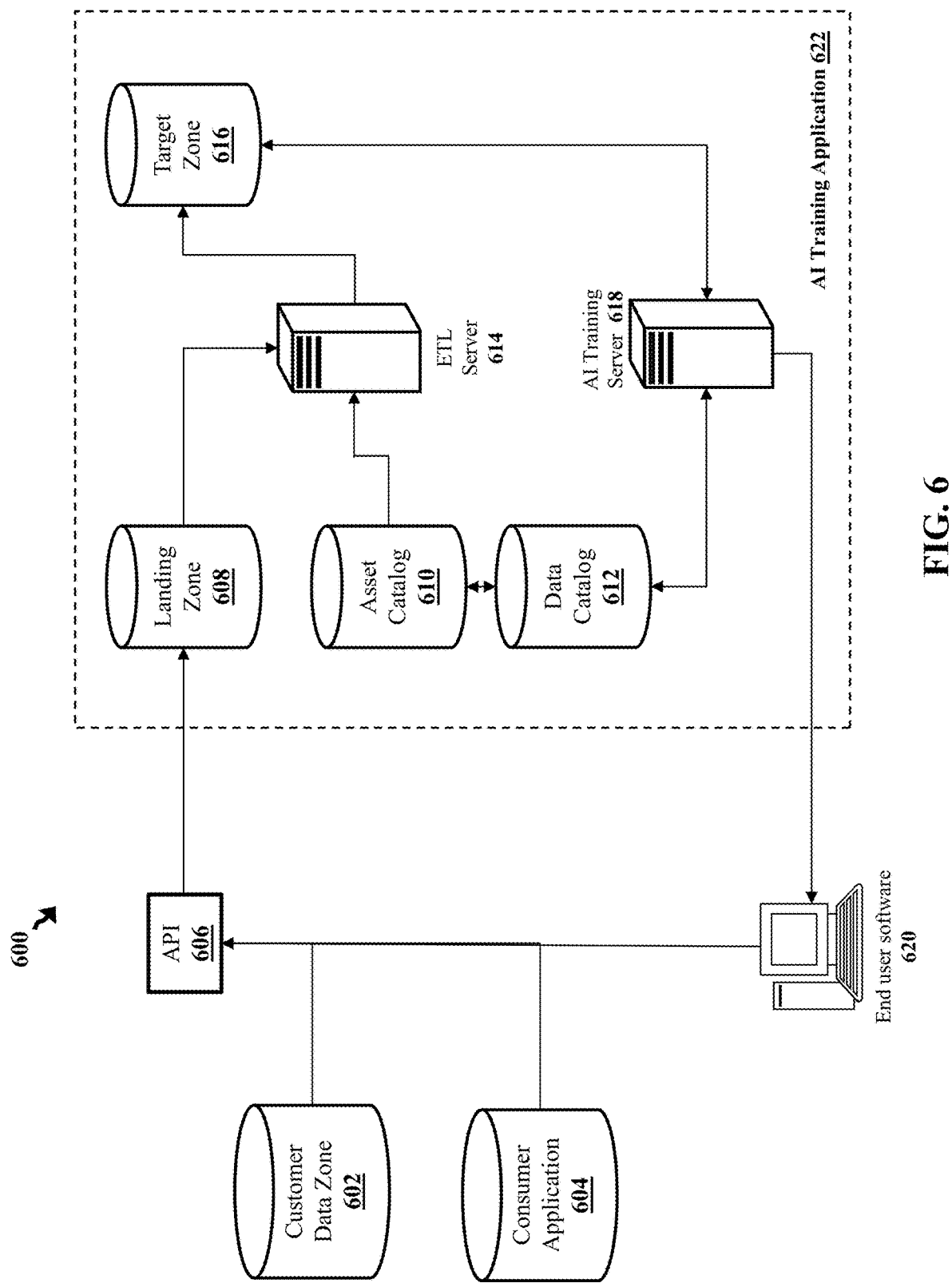
FIG. 6 illustrates a non-limiting example of components of an AI training system.

FIG. 6 depicts a schematic architecture 600 in which an AI training application 622, such as the AI training application discussed in FIGS. 4-5 or the analytics server discussed in FIGS. 1-2, can train an AI model using the methods described herein. The AI training application 622 utilizes different applications and data repositories depicted herein to train and iteratively retrain the AI model. In the architecture 600, the AI training application 622 trains an AI model that receives data from a customer data zone 602, a consumer application 604, and/or end user software 620. The customer data zone 602 may be a database that includes customer data (e.g., patient data, treatment data, and other medical information). The consumer application 604 may be a database that includes treatment data retrieved from other consumer applications (e.g., software used by doctors).

The AI training application 622 may be implemented on a cloud infrastructure, such that it can be ingested into different system architectures and existing infrastructures. For instance, because the AI training application 622 is separated and implemented on the cloud, it can be connected to any data repository to train one or more AI models using the data without being part of the infrastructure itself. For instance, as depicted, the training methods described herein can be provided as a software as a service (SaaS) without requiring the AI training application 622 to be a part of the infrastructure that includes the customer data zone 602, consumer application 604, and/or the end user software 620. As a result, the AI training application 622 can be implemented, such that the AI training methods are data, AI model, and software agnostic.

In the depicted embodiment, the AI training application 622 trains the AI model where the trained AI model may be implemented and used by any other software, such as the end user software 620. The end user software 620 may refer to any software that consumes or otherwise ingests (e.g., displays) the predicted results generated by the trained AI model. The end user software 620 may be an internal software native to the AI training application 622 or a third party software solution configured to receive the predicted results from the AI training application 622.

When the AI model is trained, the AI model can be connected to the end user software 620 where end users (e.g., physicians, medical physicists, dosimetrists, and radiation therapists) can upload images to receive predicted results. For instance, when the AI training application 622 receives an image uploaded by a doctor, the AI training application 622 executes the AI model and displays a set of predicted results on the end user software 620.

The AI training application 622 retrieves data from the customer data zone 602 and consumer application 604 and stores said data into a landing zone 608. The landing zone 608 may be a database configured to store and index data and perform various querying functions. The landing zone 608 may utilize various authentication schemes to retrieve data from the application programming interface (API) 606. The landing zone 608 may periodically retrieve data (e.g., every week or every night). Additionally or alternatively, the landing zone 608 may retrieve data upon receiving a notification from an API 606. For instance, the API 606 may monitor the data generated by the end user software 620, customer data zone 602, and the consumer applications 604. When the API 606 identifies that data (e.g., patient data, consumer data, medical professional data, and/or treatment data) has been updated (e.g., a data record has been revised or added), the API 606 may transmit a notification to the landing zone 608.

The extract, transform, and load (ETL server 614) may monitor the data within the landing zone 608. On scheduled basis (e.g., periodically, such as every night or every week), the ETL server 614 may extract the metadata (e.g., time stamp and user's interaction data) and other information (e.g., patient demographic) from the data stored within the landing zone 608. The ETL server 614 may also declassify the data by removing personally identifiable information (PII) and/or protected health information (PHI) from the data stored within the landing zone 608. Because the data within the landing zone 608 is received from different data sources, the data may be in different (and sometimes incompatible) formats. Therefore, the ETL server 614 may query various indexing and formatting models (stored within an assets catalog database 610 and/or an data catalog database 612) to create uniform data within a target zone 616 (e.g., a data repository).

The ETL server 614 may index the raw data stored within the landing zone 608 and may store longitudinal data tables within the target zone 616 that include searchable data records corresponding to the data stored within the landing zone 608. The ETL server 614 may use cataloging models and indexing protocols stored within the assets catalog database 610 and data catalog database 612. For instance, many designation information, formatting requirements, terms to be parsed, definitions, and the like may be stored in predefined and predetermined rules (specific to different clinics) stored onto the assets catalog database 610 and the data catalog database 612. In some configurations, the assets catalog database 610 may be merged with the data catalog database 612.

The longitudinal data records may include patient data, treatment data (e.g., medical images and radiation therapy treatment planning data), patient information, collaborator information (e.g., customer information), and the like. The ETL server 614 may also store feedback data within the target zone 616 including quantitative and qualitative data associated with how the predicted results were received by end users interacting with the end user software 620.

The AI training application 622 may then train one or more AI models using the data stored within the target zone 616. An AI training server 618 626 may use a variety of training methods to train the AI model using the data retrieved. For instance, the AI training server 618 626 may use regression or clustering algorithms or any other supervised, semi-supervised, and/or unsupervised method to train the AI model. In some configurations, the AI training server 618 62-6 may be a part of the AI platform and training application. In some other configurations, the AI training server 618 626 may belong to (or otherwise functionally associated with) a third party. For instance, the AI training application 622 may transmit the aggregated data to a third party, such that the third party can train the AI model. In an example, the AI training server 618 626 trains the AI model based on various images and known data retrieved from previous test cases and clinical data that has been declassified and indexed by the ETL server 614.

Upon receiving a request from the end user software 620, the AI training application 622 may execute the trained model and transmit the results to the end user software 620. The AI training application 622 may then receive data corresponding to how the predicted results were interacted with by the end users interacting with the end user software 620 and may repeat the above-described process to retain the AI model.

In an example, an AI training application includes an AI model that receives medical images and predicts the size and shape of various organs and/or abnormalities, such as a tumor. The AI training application trains the AI model based on various images and known data retrieved from previous test cases and clinical data. The AI training application first generates and initially (preliminarily) trains the AI model using images of various organs and known results inputted by various users.

When the AI model is trained, the AI training application is configured to provide an electronic platform (e.g., website or any other end-user-facing platform) where users (e.g., physicians, medical physicists, dosimetrists, and radiation therapists) can upload images and receive (e.g., view) the predicted results. For instance, the AI training application may receive the uploaded images and may execute the trained AI model to identify the size of the organs and their respective abnormalities. When the AI training application receives an image uploaded by a doctor, the AI training application executes the AI model and displays a set of predicted results on the electronic platform. The AI training application also displays a predicted outline of the shape of the organ along with predicted measurements.

Upon displaying the results, the AI training application initiates an executable file running as a background process of the doctor's computing/electronic device. As a result, the AI training application monitors the doctor's interactions with the electronic platform and determines that the doctor revises the predicted shape and size (measurements) of the organ. The AI training application identifies that the doctor spends 10 minutes revising the shape and reduces the predicted shape by a volume of 20%. The AI training application also retrieves the doctor's user profile and generates a score corresponding to the doctor's skills (e.g., doctor's experience, rank among peers, how often the doctor revises predicted results). The AI training application also displays a prompt on the doctor's electronic device requesting the doctor to rate the AI training application's prediction. The doctor inputs seven (out of 10). The AI training application stored all the above-described data as training datasets.

The AI training application may perform the above-described prediction example multiple times for various doctors and may store and/or aggregate the training datasets generated based on monitoring each doctor's interactions with the predicted results. Based on a predetermined frequency (e.g., one a month), the AI training application retrains the AI model using the datasets described above.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method for training an artificial intelligence model comprising:
   outputting, by a server onto an electronic device operated by a user, results of execution of the artificial intelligence model;
   monitoring, by the server, the electronic device to identify a set of interactions between the user and the electronic device while the electronic device is outputting the results;
   generating, by the server, a first training dataset corresponding to the user's interactions with the electronic device, the first training dataset corresponding to a frequency of correction of results and a time associated with the correction;
   generating, by the server, a second training dataset corresponding to the user's input to a prompt requesting the user to input a numerical value associated with an accuracy of the results;
   generating, by the server, a third training dataset corresponding to a score associated with the user, the server generating the score based on the user's attribute; and
   training, by the server, the artificial intelligence model using the first, second, and third training datasets, wherein the third training dataset is used to train the artificial intelligence model when the score associated with the user satisfies a threshold.

2. The method of claim 1, wherein the user's attributes comprises at least one of the user's demographic data, skills, or professional attributes.

3. The method of claim 1, wherein the first training dataset further comprises a numerical attribute corresponding to a difference between results and a second result corrected by the user.

4. The method of claim 1, wherein the server generates at least one of the first or the second training dataset periodically.

5. The method of claim 1, wherein the first training dataset further comprises at least one of a time period associated with the user interacting with the results, and a ratio of the results modified by the user.

6. The method of claim 1, further comprising:
   determining, by the server, an accuracy of the artificial intelligence model trained using the first and second training datasets, wherein when the accuracy satisfies a threshold, the server reverts to a previous version of the artificial intelligence model before the artificial intelligence model was trained using the first and second training datasets.

7. A computer system for training an artificial intelligence model, the computer system comprising:
   an electronic device configured to output results of execution of the artificial intelligence model; and
   a server communicatively coupled with the electronic device, the server configured to:
   output, onto the electronic device operated by a user, results of execution of the artificial intelligence model;
   monitor the electronic device to identify a set of interactions between the user and the electronic device while the electronic device is outputting the results;
   generate a first training dataset corresponding to the user's interactions with the electronic device, the first training dataset corresponding to a frequency of correction of results and a time associated with the correction;
   generate a second training dataset corresponding to the user's input to a prompt requesting the user to input a numerical value associated with an accuracy of the results;
   generate a third training dataset corresponding to a score associated with the user, the server generating the score based on the user's attribute; and
   train the artificial intelligence model using the first, second, and third training datasets, wherein the third training dataset is used to train the artificial intelligence model when the score associated with the user satisfies a threshold.

8. The computer system of claim 7, wherein the user's attributes comprises at least one of the user's demographic data, skills, or professional attributes.

9. The computer system of claim 7, wherein the first training dataset further comprises a numerical attribute corresponding to a difference between results and a second result corrected by the user.

10. The computer system of claim 7, wherein the server generates at least one of the first or the second training dataset periodically.

11. The computer system of claim 7, wherein the first training dataset further comprises at least one of a time period associated with the user interacting with the results, and a ratio of the results modified by the user.

12. The computer system of claim 7 the server is further configured to:
    determine an accuracy of the artificial intelligence model trained using the first and second training datasets, wherein when the accuracy satisfies a threshold, the server is configured to revert to a previous version of the artificial intelligence model before the artificial intelligence model was trained using the first and second training datasets.

13. A non-transitory machine-readable storage medium having computer-executable instructions stored thereon that, when executed by one or more processors, cause the one or more processors to perform operations comprising:
   outputting, onto an electronic device operated by a user, results of execution of an artificial intelligence model;
   monitoring the electronic device to identify a set of interactions between the user and the electronic device while the electronic device is outputting the results;
   generating a first training dataset corresponding to the user's interactions with the electronic device, the first training dataset corresponding to a frequency of correction of results and a time associated with the correction;
   generating a second training dataset corresponding to the user's input to a prompt requesting the user to input a numerical value associated with an accuracy of the results;
   generate a third training dataset corresponding to a score associated with the user, the server generating the score based on the user's attribute; and
   training the artificial intelligence model using the first, second, and third training datasets, wherein the third training dataset is used to train the artificial intelligence model when the score associated with the user satisfies a threshold.

14. The machine-readable storage medium of claim 13, wherein the user's attributes comprises at least one of the user's demographic data, skills, or professional attributes.

15. The machine-readable storage medium of claim 13, wherein the first training dataset further comprises a numerical attribute corresponding to a difference between results and a second result corrected by the user.

16. The machine-readable storage medium of claim 13, wherein the instructions further cause the one or more processors to generate at least one of the first or the second training dataset periodically.

17. The machine-readable storage medium of claim 13, wherein the first training dataset further comprises at least one of a time period associated with the user interacting with the results, and a ratio of the results modified by the user.

* * * * *